United States Patent
Vogt

(10) Patent No.: US 10,307,508 B2
(45) Date of Patent: Jun. 4, 2019

(54) VACUUM MIXING SYSTEM AND METHOD FOR THE MIXING OF POLYMETHYLMETHACRYLATE BONE CEMENT

(71) Applicant: HERAEUS MEDICAL GMBH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 709 days.

(21) Appl. No.: 14/755,137

(22) Filed: Jun. 30, 2015

(65) Prior Publication Data
US 2016/0015854 A1   Jan. 21, 2016

(30) Foreign Application Priority Data

Jul. 15, 2014  (DE) .................. 10 2014 109 905

(51) Int. Cl.
  *A61B 17/88* (2006.01)
  *A61L 24/06* (2006.01)
  (Continued)

(52) U.S. Cl.
  CPC .......... *A61L 24/06* (2013.01); *A61B 17/8827* (2013.01); *B01F 11/0054* (2013.01);
  (Continued)

(58) Field of Classification Search
  CPC ......... A61B 17/8827; A61B 2017/8838; B01F 11/0054; B01F 11/0082; B01F 13/0023;
  (Continued)

(56) References Cited

U.S. PATENT DOCUMENTS 4,671,263 A   6/1987 Draenert
4,758,096 A   7/1988 Gunnarsson
(Continued)

FOREIGN PATENT DOCUMENTS

CN   103153220 A   6/2013
CN   103801216 A   5/2014
(Continued)

OTHER PUBLICATIONS

European Search Report dated Dec. 4, 2015.
(Continued)

*Primary Examiner* — Marc C Howell
(74) *Attorney, Agent, or Firm* — Norris McLaughlin, P.A.

(57) ABSTRACT

A vacuum mixing system for the mixing of polymethylmethacrylate bone cement comprising at least one cartridge (4) having an evacuatable internal space (5) for the mixing of the bone cement, the internal space (5) of which comprises a cylindrical swept volume, a mixing element (12) that is arranged in the internal space (5) of the cartridge (4) such as to be mobile and can be operated from outside the vacuum mixing system in order to mix the content in the internal space (5) of the cartridge (4), and a dispensing plunger (2) having a cylindrical external circumference whose first base surface borders a base surface of the internal space (5) of the cartridge (4) and which can be or is locked to the cartridge (4) in detachable manner and which, in the detached state, is mobile in the cylindrical region of the internal space (5) of the cartridge (4).

18 Claims, 10 Drawing Sheets

(51) Int. Cl.
*B01F 13/00* (2006.01)
*B01F 13/06* (2006.01)
*B01F 15/02* (2006.01)
*B29B 7/24* (2006.01)
*B01F 11/00* (2006.01)
*B01F 15/00* (2006.01)
*B29K 33/00* (2006.01)

(52) U.S. Cl.
CPC ...... *B01F 11/0082* (2013.01); *B01F 13/0023* (2013.01); *B01F 13/06* (2013.01); *B01F 15/00071* (2013.01); *B01F 15/0278* (2013.01); *B01F 15/0279* (2013.01); *B29B 7/24* (2013.01); *A61B 2017/8838* (2013.01); *B01F 2215/0029* (2013.01); *B29K 2033/12* (2013.01)

(58) Field of Classification Search
CPC ............ B01F 13/06; B01F 15/0278; B01F 2215/0029; B29K 2033/12; A61L 24/06
USPC .................................................. 366/219
See application file for complete search history.

(56) References Cited

U.S. PATENT DOCUMENTS

| | | | |
|---|---|---|---|
| 4,973,168 A | 11/1990 | Chan | |
| 5,100,241 A | 3/1992 | Chan | |
| 5,344,232 A | 9/1994 | Nelson | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,033,105 A | 3/2000 | Barker et al. | |
| 6,120,174 A | 9/2000 | Hoag et al. | |
| 6,709,149 B1 | 3/2004 | Tepic | |
| 6,755,563 B2 | 6/2004 | Wahlig et al. | |
| 7,073,936 B1 | 7/2006 | Jonsson | |
| 8,757,866 B2 | 6/2014 | Vogt et al. | |
| 9,339,317 B2 | 5/2016 | Vogt et al. | |
| 2003/0075564 A1 | 4/2003 | Wahlig et al. | |
| 2010/0329074 A1* | 12/2010 | Vogt .................. | A61B 17/8825 366/190 |
| 2012/0006874 A1 | 1/2012 | Vogt et al. | |
| 2013/0145727 A1 | 6/2013 | Vogt et al. | |
| 2013/0182528 A1 | 7/2013 | Vogt et al. | |
| 2014/0126320 A1 | 5/2014 | Vogt | |

FOREIGN PATENT DOCUMENTS

| | | |
|---|---|---|
| DE | 36 40 279 A1 | 6/1987 |
| DE | 200 08 103 U1 | 9/2001 |
| DE | 698 12 726 T2 | 2/2004 |
| DE | 10 2009 031 178 B3 | 9/2010 |
| DE | 10 2010 026 497 B4 | 1/2012 |
| DE | 10 2010 026 496 B4 | 5/2014 |
| DE | 10 2012 024 710 A1 | 5/2014 |
| EP | 0 692 229 A1 | 1/1996 |
| EP | 1 005 901 A2 | 6/2000 |
| EP | 1 016 452 A2 | 7/2000 |
| EP | 1 020 167 A2 | 7/2000 |
| EP | 2 730 332 A2 | 5/2014 |
| JP | 2014-121520 A | 7/2014 |
| WO | 94/26403 A1 | 11/1994 |
| WO | 99/67015 A1 | 12/1999 |

OTHER PUBLICATIONS

English Translation of Chinese Office Action for corresponding Chinese Application No. 201510414336.7 dated May 10, 2017.
Japanese Office Action and English Translation for corresponding Japanese Application No. 2015-125452 dated Aug. 9, 2016.

* cited by examiner

VACUUM MIXING SYSTEM AND METHOD FOR THE MIXING OF POLYMETHYLMETHACRYLATE BONE CEMENT

This application claims foreign priority benefit under 35 U.S.C. § 119 of German Patent Application No. 10 2014 109 905.2 filed Jul. 15, 2014, the disclosure of which is incorporated herein by reference.

The invention relates to a vacuum mixing system for the mixing of polymethylmethacrylate bone cement (PMMA cement) from two starting components, in particular for the mixing of a medical bone cement, and for storage of the starting components.

The invention further relates to a method for the mixing of polymethylmethacrylate bone cement.

Accordingly, the subject matter of the invention is a vacuum mixing system for the storage, mixing, and, if applicable, dispensing of polymethylmethacrylate bone cement.

BACKGROUND OF THE INVENTION

Polymethylmethacrylate (PMMA) bone cements are based on the pioneering work of Sir Charnley. PMMA bone cements consist of a liquid monomer component and a powder component. The monomer component generally contains the monomer, methylmethacrylate, and an activator (N,N-dimethyl-p-toluidine) dissolved therein. The powder component, which is also referred to as bone cement powder, comprises one or more polymers, a radiopaquer, and the initiator dibenzoylperoxide. The polymers of the powder component are produced on the basis of methylmethacrylate and comonomers, such as styrene, methylacrylate or similar monomers by means of polymerisation, preferably by suspension polymerisation. During the mixing of powder component and monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Methylmethacrylate is the monomer used most commonly in polymethylmethacrylate bone cements. Redox initiator systems usually consist of peroxides, accelerators and, if applicable, suitable reducing agents. Radicals are formed only if all ingredients of the redox initiator systems act in concert. For this reason, the ingredients of the redox initiator system in the separate starting components are arranged appropriately such that these cannot trigger a radical polymerisation. The starting components are stable during storage provided their composition is adequate. Only when the two starting components are mixed to produce a cement dough, the ingredients of the redox initiator system, previously stored separately in the two pastes, liquids or powders react with each other forming radicals which trigger the radical polymerisation of the at least one monomer. The radical polymerisation then leads to the formation of polymers while consuming the monomer, whereby the cement dough is cured.

PMMA bone cements can be mixed by mixing the cement powder and the monomer liquid in suitable mixing beakers with the aid of spatulas. One disadvantage of said procedure is that air inclusions may be present in the cement dough thus formed and can cause destabilisation of the bone cement later on. For this reason, it is preferred to mix bone cement powder and monomer liquid in vacuum mixing systems, since mixing in a vacuum removes air inclusions from the cement dough to a large extent and thus achieves optimal cement quality. Bone cements mixed in a vacuum have clearly reduced porosity and thus show improved mechanical properties. A large number of vacuum cementing systems have been disclosed of which the following shall be listed for exemplary purposes: U.S. Pat. Nos. 6,033,105 A, 5,624,184 A, 4,671,263 A, 4,973,168 A, 5,100, 241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, U.S. Pat. No. 5,344,232 A. An external vacuum pump is connected In the vacuum cementing systems thus specified to generate the negative pressure.

Cementing systems, in which both the cement powder and the monomer liquid are already packed in separate compartments of the mixing systems and are mixed with each other in the cementing system only right before application of the cement, are a development of cementing technology. Said full-prepacked mixing systems were proposed through EP 0 692 229 A1, DE 10 2009 031 178 B3, U.S. Pat. Nos. 5,997,544 A, 6,709,149 B1, DE 698 12 726 T2, and U.S. Pat. No. 5,588,745 A. Patent DE 10 2009 031 178 B3 discloses a closed vacuum mixing system having a two-part dispensing plunger for closure of a cement cartridge. A combination of a gas-permeable sterilisation plunger and a gas-impermeable sealing plunger is used in this context. This principle of a closed vacuum mixing system is implemented in the closed cementing system, PALACOS® PRO, made and distributed by Heraeus Medical GmbH.

Accordingly, it is the object of the invention to overcome the disadvantages of the prior art. In particular, a closed vacuum mixing system of a simple design and inexpensive to manufacture for polymethylmethacrylate bone cement and a method for the mixing of the two component bone cement in a vacuum are to be provided. An alternative solution shall be provided as well this context. Preferably, the vacuum mixing system is to have as few mobile parts as possible. In particular, the dispensing plunger is to have a simple design as well. The vacuum mixing system shall be easy and intuitive to operate.

Said vacuum mixing system is to contain a cement cartridge, in which the cement powder is stored, as well as a separate reservoir container in which the monomer liquid is present. Accordingly, the monomer liquid is stored separate from the cement powder. Any contact of the medical users with said components shall be excluded before and after the mixing of the two cement components, i.e. the cement powder and the monomer liquid. Therefore, the reservoir container must be opened and the monomer must be transferred in a closed system. The cement powder must not contact the medical user either. During an ethylene oxide sterilization of the vacuum mixing system, it is inevitable that the ethylene oxide penetrates into and then exits from the cement powder present in the cement cartridge. The cartridge must have an opening to the ambient atmosphere with a large gas exchange surface for said gas exchange. However, this cement powder must not exit from the cement cartridge during this process. This means that the vacuum mixing system must be designed appropriately such that a gas exchange is feasible with no cement powder exiting. Moreover, it must be possible to close the cement cartridge during the mixing process in vacuum-tight manner. It is therefore the object of the invention to provide a vacuum mixing device which reconciles the contradiction that exists between the maximal gas permeability of the cement cartridge for gas exchange during the ethylene oxide sterilization and concurrent prevention of the exit of cement powder as well as the vacuum tightness of the cement cartridge during the mixing process. The vacuum mixing system to be developed shall be made, if possible, from common thermoplastic materials by means of injection moulding and thus shall be suitable for single-use applications.

Moreover, a device that is inexpensive to manufacture and working reliably for the mixing of a medical cement and, if applicable, for storage of the starting components, and a method for the mixing of the bone cement is to be devised, in which a simple manual operation can be used to mix the starting components, if possible without air inclusions arising in the cement dough.

The main component of the polymethylmethacrylate bone cement shall be a powder and the second component shall be present in the form of a liquid. Preferably, it shall be possible to store the two starting components of the bone cement separate from each other in the vacuum mixing system and to combine them safely through the use of the device.

SUMMARY OF THE INVENTION

The objects of the invention are met by a vacuum mixing system for the mixing of polymethylmethacrylate bone cement comprising at least one cartridge having an evacuatable internal space for the mixing of the bone cement, whereby the internal space comprises a cylindrical swept volume, a mixing element that is arranged in the internal space of the cartridge such as to be mobile and can be operated from outside the vacuum mixing system in order to mix the content in the internal space of the cartridge, and a dispensing plunger having a cylindrical external circumference whose first base surface borders a base surface of the internal space of the cartridge and which can be or is locked to the cartridge in detachable manner and which, in the detached state, is mobile in the cylindrical region of the internal space of the cartridge, whereby a gas-permeable and particle-impermeable feedthrough is arranged in the dispensing plunger or a feedthrough is formed between the dispensing plunger and the internal wall of the internal space, whereby the feedthrough extends from an opening in the jacket surface of the dispensing plunger to an opening in the first base surface of the dispensing plunger.

DETAILED DESCRIPTION

A cylinder in the scope of the present invention and according to general definition is a body bounded by two parallel, planar, congruent surfaces (base surface and cover surface) and a jacket surface and/or cylinder surface, whereby the jacket surface is formed by parallel straight lines. This means that the cylinder is generated through shifting a planar surface along a straight line that is not positioned in said plane. The height of the cylinder is given by the distance between the two planes, in which base surface and cover surface are situated.

If the straight lines are perpendicular to base surface and cover surface, the structure is called a straight cylinder. The straight cylindrical geometry of the internal space is preferred according to the invention, but particularly preferably relates only to one or more partial region(s) of the entire internal space of the cartridge. Accordingly in the scope of the present invention, a straight circular cylinder simply is a special case of cylindrical geometry though it is a particularly preferred symmetry as it is particularly easy to produce.

A cylindrical external circumference of the dispensing plunger presently shall be understood to mean that the dispensing plunger, at least a section there are, comprises a cylindrical circumference that forms the maximum radial extension with respect to the dispensing plunger relative to the cylindrical geometry of the cylindrical section. Regions of the dispensing plunger can just as well be of a shape different from cylindrical shape, in particular at least one sealing ring, at least one snap-in means or opposite snap-in means, and a wiper lip can be present in addition to the opening in the jacket surface. Preferably, the dispensing plunger seals the cylindrical swept volume, except for the feedthrough and a vacuum connector, by means of the cylindrical external circumference when the cylindrical external circumference is arranged inside the swept volume.

If a feedthrough is formed between the dispensing plunger and the internal wall of the internal space, a groove bordering the feedthrough can be provided, for example, in the cylinder jacket of the dispensing plunger and/or in the internal wall of the internal space. In this context, the feedthrough refers to the dispensing plunger touching against the internal walls of the internal space. The feedthrough in the openings can therefore also be defined by the regions on which the dispensing plunger does not touch against the internal walls of the internal space, which can also be defined, for example, by a depression, a furrow or groove in the otherwise cylindrical internal wall of the cartridge. However, the feedthrough is preferred to be arranged in the dispensing plunger.

Presently, negative pressure shall be understood to mean a pressure related to the ambient atmosphere that is less than the ambient atmospheric pressure.

The bone cement is particularly preferred to be a PMMA bone cement. Preferably, the polymethylmethacrylate bone cement (PMMA bone cement) is mixed and/or can be produced from at least two components. Particularly preferably, one component is liquid and the other component is powdered.

The cylindrical region of the sweat volume of the dispensing plunger can also have depressions, such as a notch, or projections, such as a spring or a circumferential ring, arranged on it such that the cylindrical symmetry can be disrupted regionally. As a result, a snap-in mechanism for snap-means can be implemented on the dispensing plunger in the cylindrical region. The same applies accordingly to the cylindrical external circumference of the dispensing plunger.

Preferably, the vacuum mixing system is provided to be gas-tight with respect to the outside and/or can be sealed to be gas-tight.

A refinement of the invention proposes that the dispensing plunger comprises at least one circumferential seal that seals the internal space of the cartridge with respect to the outside, whereby it is preferred to have at least one circumferential seal arranged between a second base surface of the dispensing plunger, which is situated opposite from the first base surface of dispensing plunger, and the opening in the jacket surface of the dispensing plunger.

As a result, the vacuum stability of the internal space is improved. This allows the negative pressure or vacuum in the internal space to be maintained for longer periods of time.

A variant of an embodiment of the present invention can provide one of the jacket surfaces of the cartridge wall of the cartridge to comprise an opening, which overlaps with the opening in the jacket surface of the dispensing plunger while the dispensing plunger is in an opened position, and by means of which the internal space is or can be connected in gas-permeable manner to the surroundings of the vacuum mixing system.

As a result, the dispensing plunger can be inserted deep and stable into the cartridge. This allows better stability of the vacuum mixing system to be attained and the dispensing plunger does not become lodged as easily can be designed to be somewhat shorter.

In this context, the invention can provide a closure element to be arranged on the external wall of the cartridge by means of which the opening in the wall of the cartridge can be closed, preferably a closure element to be arranged on the external wall of the cartridge that can be shifted in axial direction of the cartridge.

As a result, the opening of the cartridge will does not need to be closed by the dispensing plunger or at least not by the dispensing plunger alone. Moreover, the closure element arranged on the outside of the cartridge wall shuts by itself upon the action of the vacuum in the interior of the internal space and thus seals the opening of the cartridge wall. Alternatively, the dispensing plunger can be twisted and/or shifted appropriately with respect to the opening of the cartridge wall such that the feedthrough no longer overlaps with the opening in the cartridge wall and thus the feedthrough is and/or can be closed in or on the dispensing plunger.

The embodiment having a closure element on the external wall of the cartridge can be provided such that the closure element is a circumferential cuff that touches, to fit, against the external wall of the cartridge and can be shifted in axial direction of the cartridge in order to cover and thus close the opening in the wall of the cartridge, whereby, preferably, at least one handle part is fastened on the cuff and is provided for manual shifting of the cuff on the external wall of the cartridge.

The cuff does not have to be fully circumferential, but can be interrupted, that means it can have an axial discontinuity. For this purpose, the cuff can be provided as a ring segment or tube segment that surrounds the external wall of the cartridge by at least 50%, preferably by at least 60%, particularly preferably by at least 75%. Preferably, the internal diameter of the cuff is the same or smaller than the external diameter of the cartridge. This embodiment is particularly easy and inexpensive to implement.

An alternative embodiment of the present invention can provide the dispensing plunger, in a first lockable position, to project from the cartridge such that the opening in the jacket surface of the dispensing plunger is open, and can provide the dispensing plunger, in a second lockable position, to be arranged deeper in the internal space of the cartridge such that the opening in the jacket surface of the dispensing plunger is closed by the internal wall of the cartridge.

Said embodiment is advantageous in that the cartridge wall can be made without an opening.

In this context, the invention can provide a circumferential sealing element to be arranged between the opening in the jacket surface of the dispensing plunger and the second base surface of the dispensing plunger, which is situated opposite from the first base surface of the dispensing plunger.

As a result, sealing of the internal space of the cartridge in the various positions of the dispensing plunger is ensured.

Preferred embodiments of the invention can be characterised in that a gas-permeable particle filter, in particular a pore filter, is arranged in the feedthrough and/or at the opening to the feedthrough in the jacket surface of the dispensing plunger and/or at the opening to the feedthrough in the first base surface of the dispensing plunger, whereby the gas-permeable particle filter is preferred to be impermeable for particles having a diameter of more than 1 µm, particularly preferably for particles having a diameter of more than 5 µm.

This ensures that the cement powder from the internal space of the cartridge remains in the internal space, whereas gases can be evacuated from the internal space and other gases, such as, for example, ethylene oxide can be filled into it.

According to a refinement, the present invention proposes the dispensing plunger to be gas-tight on its side that points from the interior of the cartridge, except for a vacuum feedthrough.

The vacuum feedthrough can then be used to draw a vacuum in the inside of the cartridge once the feedthrough has been closed.

Moreover, the invention can provide the dispensing plunger to comprise, on the first base surface, a gas-permeable pore disk that is supported by ribbing. This allows the pore disk to be stabilised mechanically.

According to a further embodiment, the invention can provide that the dispensing plunger can be pushed axially into the cartridge in order to dispense a bone cement dough, that has been mixed from a bone cement powder and a monomer liquid, through a dispensing opening on an end of the cartridge opposite from the dispensing plunger, whereby the dispensing plunger preferably can be pushed axially into the cartridge after detaching a locking mechanism.

This ensures that the dispensing plunger can be used for its actual purpose, namely the dispensing of the cement dough from the cartridge, after the sterilisation of the content of the internal space and after the mixing of the bone cement components in a vacuum.

The invention also proposes that a dispensing opening of the cartridge comprises a connecting means, in particular a connecting thread.

A connecting thread in the form of an internal thread or external thread is particularly suitable as connecting means. The connecting thread can be used, on the one hand, to close an application tube and, on the other hand, to fasten the cartridge on a base or a base element.

Preferably, the invention can just as well provide the mixing element to be arranged on a rod that is guided through a gas-tight passage into the interior of the cartridge, and the mixing element to be mobile by pushing it in and out of the cartridge and by rotating it in the cartridge, whereby the rod is preferred to comprise a predetermined breakage site at which the rod can be broken off near the passage once it has been pulled out of the cartridge.

With the rod being passed through, the mixing element is particularly easy to operate from outside. Preferably, the rod is guided through a gas-tight passage in the dispensing plunger into the inside of the cartridge.

Preferred embodiments can be characterised in that the vacuum mixing system comprises a reservoir container for monomer liquid, in particular comprises a glass container for monomer liquid, in that the cartridge contains a cement powder, whereby an opening element for opening of the reservoir container is provided, and the cartridge is or can be connected via a conduit to the opened reservoir container.

The term "opening element" shall be understood to mean devices, which, when actuated, can cause the reservoir container of the monomer liquid to be opened. Exemplary opening devices a specified in DE 10 2010 026 497 B4 and DE 10 2010 026 496 B4.

It is a crucial advantage of glass ampoules, as reservoir containers, that these are fully diffusion-proof and therefore impermeable for the monomer liquid. As a result, the monomer liquid can be stored for several years at temperature without any losses.

In this context the invention can provide the vacuum mixing system to comprise a base element, whereby the base element stores the cartridge, the reservoir container, and the opening element.

The base element and/or the base integrates cartridge and further components the can be connected to the cartridge. Moreover, the base element can be used to set-up the vacuum mixing system in stable manner.

In this context, the invention can provide the base element to comprise a coupling means for a non-positive fit- and/or positive fit-like connection to the cartridge, in particular to the connecting means on the dispensing opening of the cartridge.

This allows a stable and tight connection of the cartridge to the base element to be detained.

The invention can just as well provide a valve element controlling and/or triggering the outflow of the monomer liquid from the reservoir container into the cartridge to be arranged in the conduit.

By this means, the monomer and/or the second cement component can be prevented from inadvertently and prematurely mixing, which might lead to chemical curing of the cement in the cartridge and ensuing blockage of the vacuum mixing system.

Vacuum mixing systems according to the invention characterised in that a snap-in means is provided on the cartridge and at least one opposite snap-in means is provided on the dispensing plunger, whereby the dispensing plunger is detachably locked to the snap-in means in the cartridge in one position or is detachably locked in at least two positions, whereby the feedthrough is opened in a first locked position and is closed in gas-tight manner in a second locked position.

As a result, it can be insured that the snap in dispensing plunger is not inadvertently move in response to the effect of the vacuum. When the dispensing plunger is detached, the dispensing plunger can be moved in targeted manner by the vacuum. When the dispensing plunger is locked in the second position or the feedthrough is closed by the closure element, the vacuum can be used (through the vacuum connector in the dispensing plunger) to aspirate the monomer liquid and/or the second liquid cement component into the cartridge such that it can be mixed therein with the cement powder inside the cartridge by means of the mixing element.

The underlying objects of the invention are also met by a method for the mixing of polymethylmethacrylate bone cement in a cartridge of a vacuum mixing system, in particular of a vacuum mixing system according to the invention, in which an internal space of a cartridge that is closed by a dispensing plunger is opened by a gas-permeable feedthrough in the dispensing plunger, whereby gas is evacuated from the internal space and the internal space is filled with a sterilising gas, whereby subsequently the feedthrough is closed by shifting the dispensing plunger or is closed by operating a closure element on the external circumference of the cartridge, followed by evacuating the internal space through a vacuum feedthrough and followed by mixing starting components of the bone cement with a mixing element in the internal space of the cartridge in a vacuum.

In this context, the invention can provide the dispensing plunger to be locked to the cartridge after the insertion of dispensing plunger into the cartridge and/or the dispensing plunger to be locked after the shifting of the dispensing plunger such that it is not drawn into the cartridge in response to the effect of the negative pressure, and the locking to be detached after the bone cement is mixed and the mixed bone cement dough to be expelled from the cartridge by propelling the dispensing plunger in the internal space of the cartridge through an opposite dispensing opening.

Moreover, the invention can provide the internal space of the cartridge to contain a cement powder, a monomer liquid to be supplied into the internal space of the cartridge, preferably to be aspirated into the internal space of the cartridge by the negative pressure, and the monomer liquid to be mixed with the cement powder in be evacuated internal space of the cartridge.

The invention is based on the surprising finding that, having a feedthrough in or on the dispensing plunger, which is connected to an opening in the jacket surface of the working plunger and with an opening in the first base surface of the cylindrical dispensing plunger oriented at the internal space, allows the internal space of a cartridge for the mixing of bone cement to be made accessible from outside for an evacuation and a sterilization by a gas (such as ethylene oxide), and, concurrently, the option to close the feedthrough allows to make the internal space evacuatable through an additional vacuum feedthrough at ambient monomer pressure such that the content can be mixed in response to the effect of a vacuum. The opening to the internal space can be sealed simply by shifting or twisting the dispensing plunger or by means of a closure element on the external wall of the cartridge. As a result, the vacuum mixing system according to the invention is particularly easy to use and operate, whereby the design is easy to implement and inexpensive to realise.

A closed vacuum mixing system according to the invention is composed, for example, of a cement cartridge, in which a mixing element is arranged, whereby the mixing element can be axially moved by means of an actuation rod that is guided out on a first cement cartridge end, and the first cement cartridge end is closed by a cylinder-shaped dispensing plunger. The vacuum mixing system is characterised in that a) at least one opening in the cartridge wall is arranged at the first cement cartridge end;

b) a closure element is arranged on the external wall of the cement cartridge that can be shifted and has a length in axial direction at least equal to the axial length of the at least one opening in the cartridge wall, and c) the dispensing plunger possesses at least one opening in the cylinder-shaped jacket surface.

The cement cartridge is a cartridge that is well-suited for storing a cement component and for mixing a cement dough.

The opening in the cartridge wall can be provided to be circular, elliptical or rectangular. Besides, any regular or irregular-shaped openings are well-suited as well.

The shiftable closure element is provided as a hollow cylinder or as a hollow cylinder having an axial discontinuity, whereby the hollow cylinder has an internal diameter that is equal to or smaller than the external diameter of the cement cartridge. The closure element in the non-closed state can be arranged below the at least one opening in the jacket surface of the cement cartridge. In this state, ethylene oxide can flow through the opening into the interior of the cement cartridge and exit again once the sterilization is completed. When the closure element is being pushed axially over the at least one opening such that said one opening is fully covered, the internal space of the cement cartridge is closed in gas-tight manner.

The vacuum mixing system according to the invention can be characterised, for example, in that the cylinder-shaped dispensing plunger a) is provided to be gas-tight on its top;
b) possesses a vacuum connector on the top;
c) possesses a gas-permeable pore disk on the bottom that is supported by a ribbing;
d) an internal space that is formed by the gas-tight top, the ribbing of the pore disk, and the internal cylindrical jacket surface;
e) the vacuum connector is connected to the internal space in gas-permeable manner; and in that
f) at least one opening is arranged on the jacket surface and has an axial length that is smaller than or equal to the distance between the gas-tight top and the ribbing, whereby the at least one opening is connected, in gas-permeable manner, to the pore disk via the internal space.

Preferably, the dispensing plunger of the vacuum mixing system is detachably arranged in the cement cartridge in appropriate manner such that the at least one opening of the cylindrical jacket surface of the dispensing plunger overlaps with the at least one opening of the cements cartridge wall at least partly. As a result, during the sterilisation with ethylene oxide, the gas can enter into the interior of the cement cartridge through the overlapping openings. After completion of the sterilization, the remaining ethylene oxide can exit from the cement cartridge through these overlapping openings. In this context, the large surface of the facilitates the exiting of the gas.

It is essential for the function of a vacuum mixing system having a shiftable closure element that the closure element fully covers the at least one opening in the cement cartridge wall after the shift onto the first cement cartridge end. As a result, the internal space of cement cartridge is closed in gas-tight manner. Accordingly, upon application of the vacuum to the vacuum connector on the top of the dispensing plunger, a vacuum can be generated in the internal space of the cement cartridge without any air being able to flow into the cement cartridge from outside. The vacuum in the interior of the cement cartridge aspirates the closure element onto the cement cartridge. As a result, the closure element is pressed against the external wall of the cement cartridge and the gas-tight seal is reinforced. Accordingly, as an alternative, the closure element can be arranged on the outside the cartridge such that it can rotate, whereby the closure element, in a first position, leaves the opening open and, in a second, rotated position, closes the opening.

It is advantageous that the rod and/or the actuation rod for the mixing element comprises a predetermined breakage site. Preferably, the actuation rod is guided through a gas-tight feedthrough in the dispensing plunger such that it can rotate and is axially mobile in longitudinal direction. Said predetermined breakage site is arranged appropriately such that the mixing element touches against the bottom of the dispensing plunger after the actuation rod is pulled upwards out of the cartridge in the direction of the dispensing plunger, and the actuation rod can be broken off right at the upper edge of the dispensing plunger. As a result, it is easy to use the pestles of common manually operated dispensing devices to move the dispensing plunger axially in the direction of the cartridge head, whereby the cement dough is extruded from the opposite dispensing opening.

An exemplary vacuum mixing system according to the invention is composed of a reservoir container for the monomer liquid, a cement cartridge filled with cement powder, an opening element for opening the reservoir container, and a base element, whereby the cement cartridge, the reservoir container, and the opening element are stored in the base element. This means that the base element connects the cement cartridge, the reservoir container, and the opening element to each other.

For this purpose, the base element of the vacuum mixing system according to the invention advantageously contains a coupling means for a non-positive fit-like and/or positive fit-like connection to the cement cartridge, in particular to the dispensing opening of the cement cartridge. The coupling means of the base element can be provided, for example, as a cylinder having an external thread. The dispensing opening of the cement cartridge can contain an internal thread such that the cement cartridge can be screwed onto the external thread of the cylinder of the base element. As a result, the cement cartridge can be connected to the base element in liquid-tight manner. In turn, the base element can contain an injection nozzle for introducing the monomer liquid into the cement powder that is stored in the cement cartridge.

Preferably, a conduit means and/or a conduit is arranged in the base element of the vacuum mixing system according to the invention. The conduit means connects the reservoir container into the cement cartridge in appropriate manner such that the monomer liquid can flow through the conduit means into the reservoir container after the reservoir container is opened by actuating the opening element. Preferably, the monomer liquid is aspirated from the reservoir container through the conduit means into the cement cartridge by the effect of a vacuum.

Similar designs, such as the beveling of the region of the base surface of the dispensing plunger facing the internal space or placing a pore filtering of the opening in the cartridge wall, are more elaborate and/or less favourable to implement, but still implement the present invention.

BRIEF DESCRIPTION OF THE DRAWINGS

Further exemplary embodiments of the invention shall be illustrated in the following on the basis of ten figures, though without limiting the scope of the invention. In the figures.

Openings, feedthroughs, internal spaces, and free spaces, i.e. non-physical parts that are defined by a surrounding shape only a marked by arrows as reference arrows in FIGS. 1 to 10, whereas all physical components and features of the vacuum mixing systems according to FIGS. 1 to 10 are identified by reference lines that end at the corresponding components and/or features.

Figure 1:
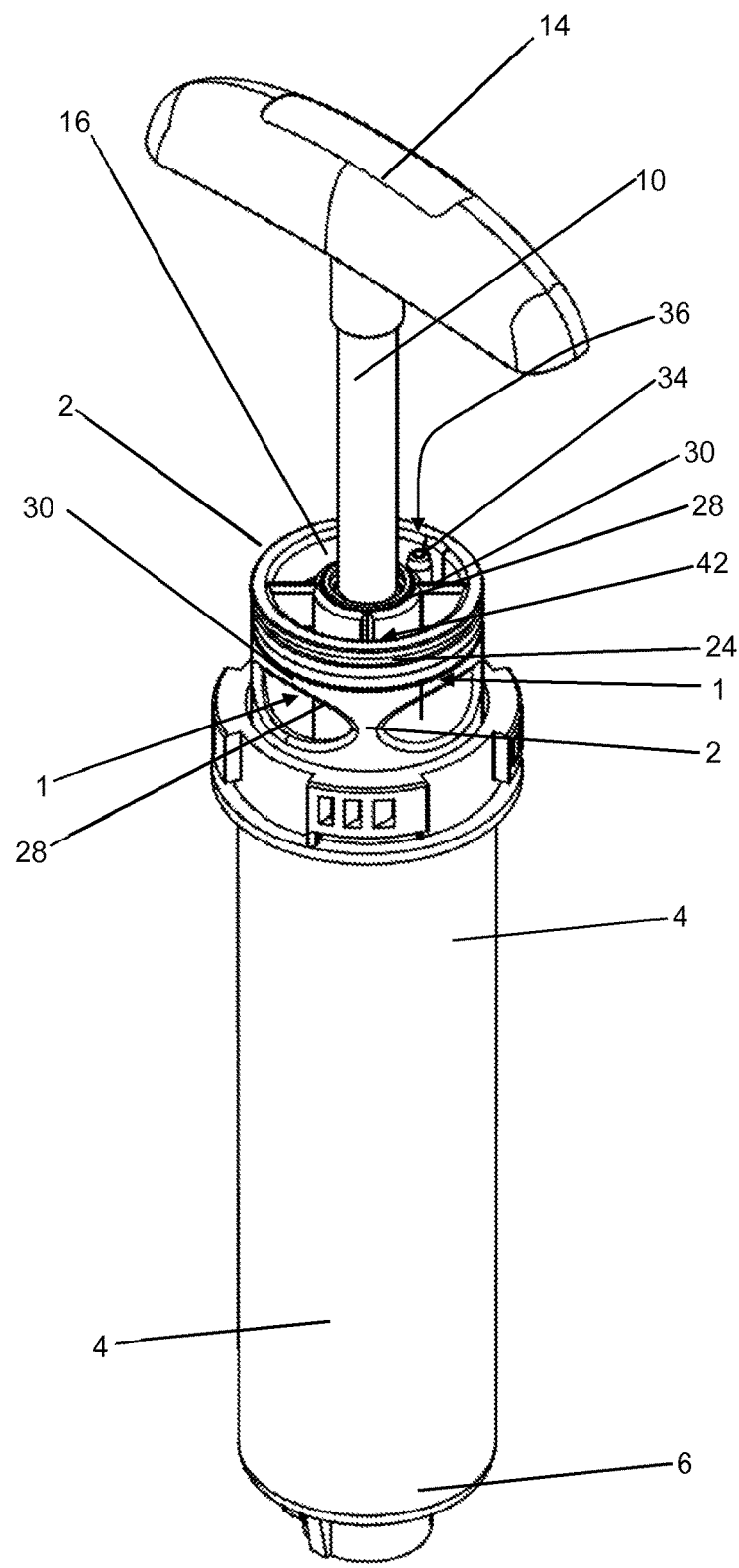
FIG. 1: shows a perspective external view of a vacuum mixing system according to the invention with open feedthrough.
Figure 2:
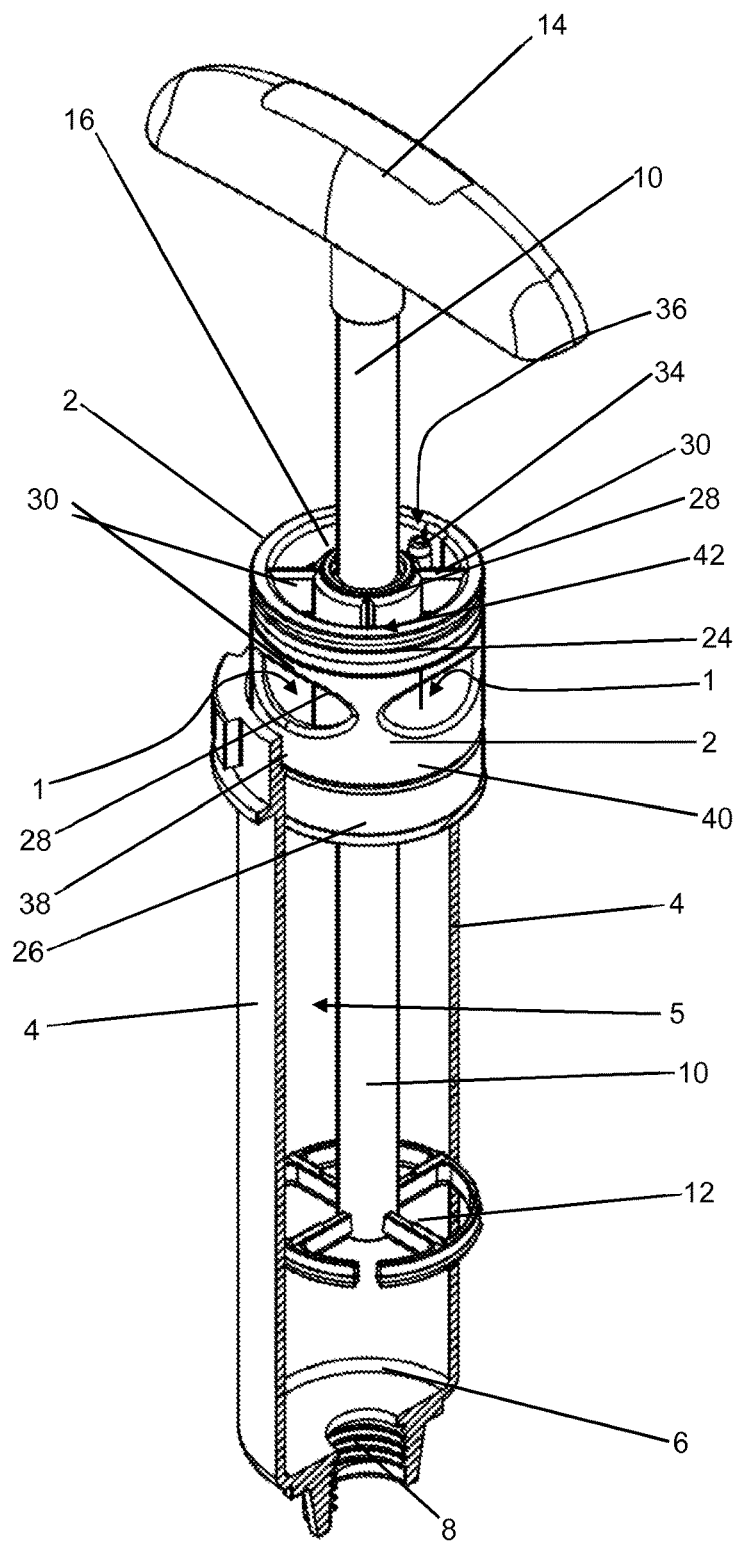
FIG. 2: shows a perspective partial sectional view of the vacuum mixing system according to FIG. 1 with open feedthrough.
Figure 3:
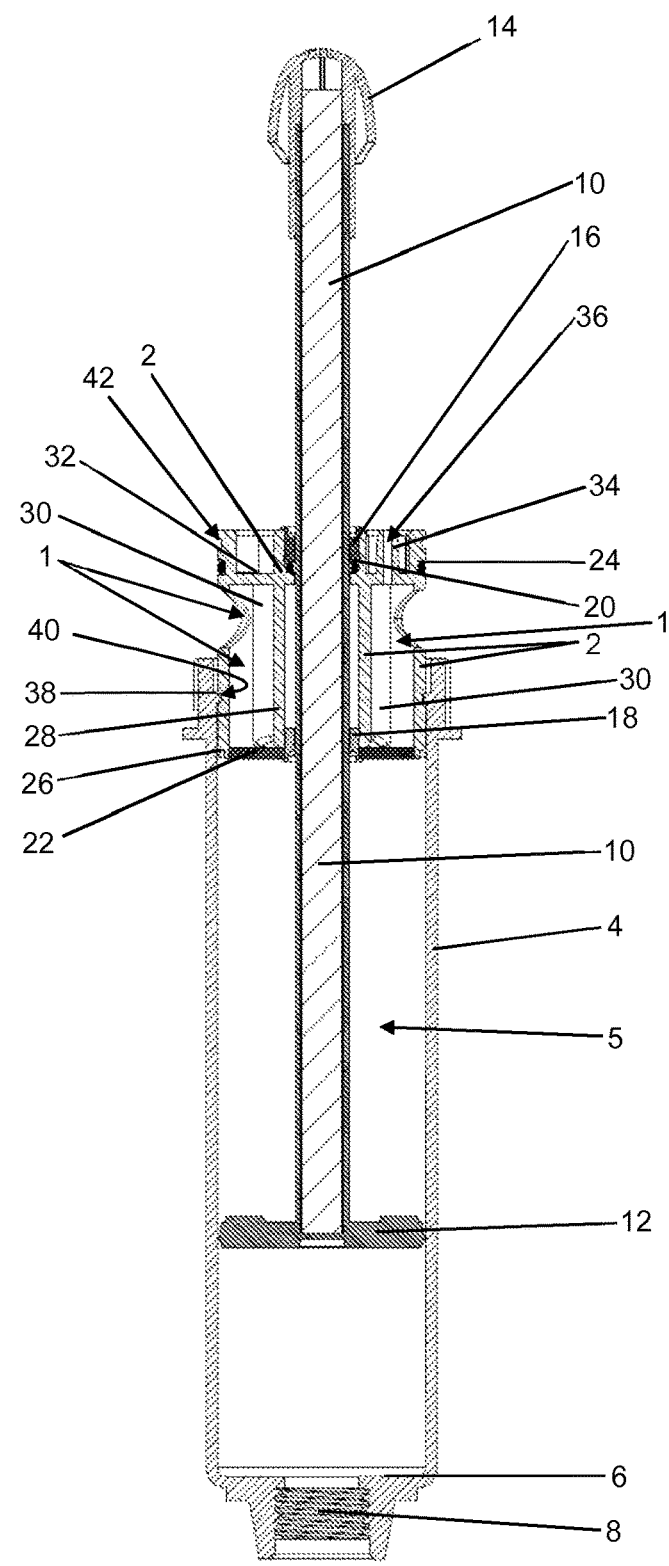
FIG. 3: shows a cross-sectional view of the vacuum mixing system according to FIGS. 1 and 2 with open feedthrough.
Figure 4:
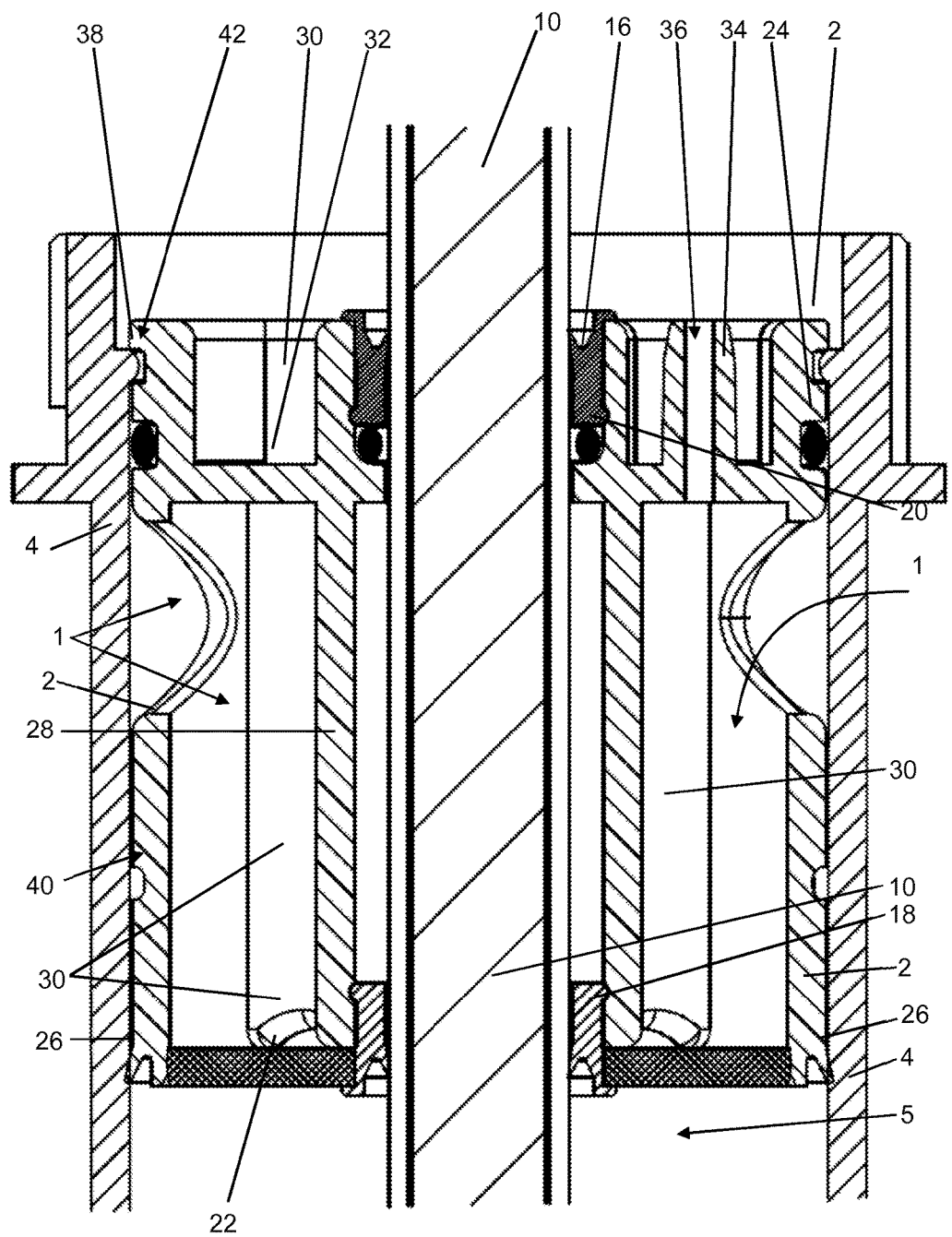
FIG. 4: shows a cross-sectional view of a detail of the vacuum mixing system according to FIGS. 1, 2 and 3 with closed feedthrough.

FIGS. 1 to 3 show a first exemplary embodiment of the present invention and/or a first vacuum mixing system according to the invention, in which a feedthrough 12 through a largely cylindrical dispensing plunger 2 is open, and FIG. 4 shows the same exemplary embodiment of the present invention and/or the first vacuum mixing system according to the invention, in which the feedthrough 1 through the dispensing plunger 2 is closed. In this context, FIG. 1 shows a perspective external view, FIG. 2 shows a perspective partial sectional view, FIG. 3 shows a cross-sectional view, and FIG. 4 shows a cross-sectional view of a detail of the vacuum mixing system according to the invention.

The vacuum mixing system comprises a largely tube-shaped cartridge 4 having an internal space 5. The internal space 5 contains a cement powder (not shown) for producing a cement dough from two components. The cartridge 4 is closed on the front side (on the bottom in FIGS. 1 to 3 and not shown in FIG. 4) by means of a plate 6, in which an opening having an internal thread 8 is provided. A baseplate (not shown) and/or a base (not shown) or a dispensing tube (not shown) for application of the ready-mixed cement dough can be mounted to the internal thread 8. Via the baseplate and/or the base, a second liquid container (not shown) containing a liquid monomer as second liquid component of the bone cement is connected to the cartridge 4 by means of a conduit (not shown). For this purpose, the conduit merges into a socket on the baseplate and/or base, whereby an external thread is provided on the socket thread such that the cartridge 4 can be or is screwed onto the socket by means of the internal thread 8 such that the conduit from the liquid reservoir can be or is connected via the conduit to the cartridge 4 in pressure-tight manner. A vacuum mixing system having a base of this type and/or a baseplate of this type, a conduit of this type, a socket of this type, and a liquid reservoir of this type is known, for example from DE 10 2009 031 178 B3 and/or U.S. Pat. No. 8,757,866 B2, such that reference shall be made to these patents for any details. For the discussion in the following, it shall be presumed that the front side of the cartridge 4 is initially closed towards the outside by the cartridge 4 being screwed onto a base of this type and/or a baseplate of this type of the vacuum mixing system by means of the internal thread 8.

The cartridge 4 is closed on the rear side (towards the top in FIGS. 1 to 4) by means of the dispensing plunger 2. A feedthrough in the dispensing plunger 2 has a rod 10 extend through it that ends on the front side in the internal space 5 of the cartridge 4 in a mixing element 12 that comprises four mixing vanes that extend radially in the direction of the wall of the cartridge 4. The rod 10 ends, on the rear side (on the top in FIGS. 1 to 3 and not shown in FIG. 4), in a handle 14 by means of which the rod 10 can be moved by hand. The rod 10 can be rotated about its axis and is stored in axial direction (shiftable in longitudinal direction) in the dispensing plunger 2. For this purpose, two bearing rings 16, 18 are provided in the dispensing plunger 2 and touch into the fit on the rod 10 and support the rod 10 as in a bearing.

The lower bearing ring 18 also serves to seal the internal space 5 in order to prevent powder or cement dough from exiting from the internal space 5. Moreover, in order to seal the internal space 5 in gas-tight and pressure-tight manner, a seal 20 in the form of an O-ring made of rubber is provided.

Since the rod 10 can be rotated by hand and shifted axially, the content of the internal space 5 can be mixed manually by means of the mixing element 12.

The feedthrough 1 through the dispensing plunger 2 is covered on the front side of the dispensing plunger 2 by means of a pore disk 22. The pore disk 22 prevents the cement powder from entering into the feedthrough 1 and/or the cement powder from exiting from the vacuum mixing system.

The external circumference of the dispensing plunger 2 has a circumferential seal 24 provided on it in the form of an O ring made of rubber by means of which the intervening space between the dispensing plunger 2 and the internal wall of the cartridge 4 is sealed and to allow the internal space 5 to be closed with respect to the outside in gas-tight and pressure-tight manner, when the dispensing plunger 2 is pushed and/or inserted deeply enough into the cartridge 4, as is shown, for example, in FIG. 4.

The dispensing plunger 2 comprises, on the front side, a circumferential wiper lip 26 by means of which, upon dispensation of a ready-mixed bone cement from the internal space 5 through the opening in the plate 6 by means of the dispensing plunger 2, all of the cement dough is propelled towards the front without any cement dough being squeezed from the internal space 5 past the wiper lip 26. The wiper lip 26 is deformed for this purpose. In this context, the wiper lip 26 does not project into the wall of the cartridge 4, as shown in FIG. 4, but is deformed accordingly with respect to its original shape that is shown in FIG. 4. Due to the elastic force arising in the process, the internal space 5 is sealed by the wiper lip 26. The same sealing principle, with respect to the rod 10 in this case, is also used for the lower bearing ring 18.

In the dispensing plunger 2, the rod 10 is guided through a sleeve 28 of the dispensing plunger 2. Four struts 30 extend radially, as part of the dispensing plunger 2, from the sleeve 28 in the direction of the external circumference of the dispensing plunger 2 The struts 30 serve for mechanical stabilisation and shaping of the dispensing plunger 2 and for positioning of the pore disk 22. The dispensing plunger 2 is closed on the rear side between the openings in the jacket surface of the dispensing plunger 2 for the feedthrough 1 and the rear-side end of the dispensing plunger 2 (on the top in FIGS. 1 to 4) by a plate 32. The plate 32 is part of the dispensing plunger 2 and both are provided as a single part.

The vacuum feedthrough 34 that merges into a vacuum connector 36 in the form of a socket 36 is provided on the plate 32. A hose (not shown) can be plugged onto the vacuum connector 36 and can be connected to a vacuum source (not shown).

A circumferential spring 38 in the form of a ring 38 is provided in the internal circumference of the cartridge 4 and is provided as snap-in means 38 for locking the dispensing plunger 2 in the cartridge 4. Two circumferential grooves 40, 42 and/or circumferential recesses 40, 42 are provided in the dispensing plunger 2 as opposite snap-in means 40, 42 such that the dispensing plunger 2 can be locked in two different positions with respect to its mobility in longitudinal direction in the cartridge 4. Instead of the system consisting of groove 40, 42 and spring 38, other locking means that can, for example, be deformed by hand and are thus easier to detach can be provided just as well without limiting the invention in any way or shape.

Initially, the bone cement powder is filled into the cartridge 4 that is closed on the front plate 6. For this purpose, the dispensing plunger 2 is not yet inserted into the cartridge 4 initially. Subsequently, the dispensing plunger 2 is plugged into the cartridge 4 until the spring 38 locks to the lower groove 40. Said first locked position of the dispensing plunger to is shown in FIGS. 1 to 3. The entire cartridge 4 and/or the entire vacuum mixing system can be disinfected and/or sterilised in a chamber through the open feedthrough 1 by evacuating the air from the surroundings of the cartridge 4 and/or of the vacuum mixing system and by filling the surroundings of the cartridge 4 and/or of the vacuum mixing system with ethylene oxide.

Subsequently, the dispensing plunger 2 is pushed more deeply into the cartridge 4 until the spring 38 engages the upper group 42 and the dispensing plunger 2 is locked in a second position. The second locked position of the dispensing plunger 2 in the cartridge 4 is shown in FIG. 4. The internal wall of the cartridge 4 closes the openings in the cylinder jacket of the dispensing plunger to twitch the passages 1 in the second position. The seal 24 closes the internal space 5, except for the vacuum feedthrough 36, in pressure-tight and gas-tight manner by the seal 24 touching against the internal walls of the cartridge 4.

A hose connected to a vacuum source is then connected to the vacuum connector 34. The air is drawn from the internal space 5 through the vacuum feedthrough 36. The pore disk 22 prevents powder from advancing from the internal space 5 into the vacuum system. Since the internal space 5 is pressure-tight, except for the conduit connected to the plate 6 and/or the internal thread 8 and the liquid container, the internal space 5 is being evacuated. The conduit and the liquid reservoir of the vacuum mixing system are closed towards the outside in gas-tight and pressure-tight manner. The monomer is aspirated from the liquid reservoir through the conduit into the internal space 5. It is mixed with the cement powder in this location.

The cement powder can be mixed by hand with the monomer liquid in a vacuum by means of the mixing element 12 in the internal space 5 by rotating and pushing the rod 10 in and pulling it out. After the mixing took place, the cartridge 4 is unscrewed from the base and/or baseplate and a dispensing tube (not shown) is screwed onto the internal thread 8. The dispensing tube can contain a static mixer. The rod 10 can be pulled out of the internal space 5 all the way to the stop such that the mixing element 12 touches against the front side of the dispensing plunger 2. The rod 10 can be broken off at a predetermined breakage site (not shown) by means of the handle 14. Subsequently, the cartridge 4 can be inserted into an extrusion device (not shown) for propelling the dispensing plunger 2 in the cartridge 4, or the dispensing plunger 2 is propelled by means of a pestle (not shown). For example, the dispensing plunger 2 can be unlocked from its second position and the dispensing plunger 2 is propelled in the cartridge 4 by the vacuum that is still being applied, since no vacuum, but rather ambient pressure, is now being applied outside the cartridge 4.

Propelling the dispensing plunger 2 causes the cement dough to be driven from the internal space 4 of the cartridge 4 and to be applied by means of the dispensing tube.

All parts of the vacuum mixing system are manufactured from plastics by injection moulding, whereby the seals 20, 24 preferably consists of rubber or another elastic plastic material.

Figure 5:
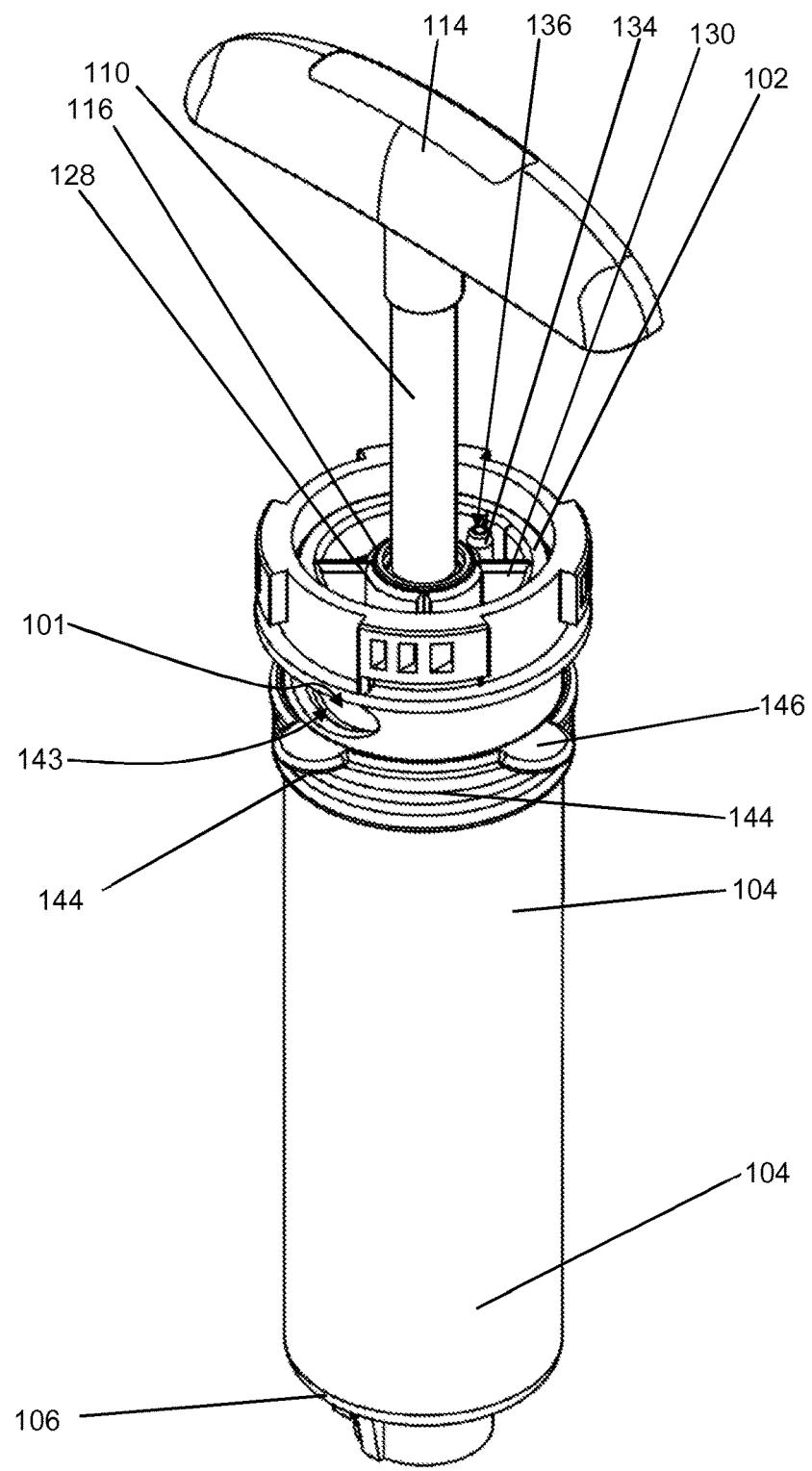
FIG. 5: shows a perspective external view of an alternative vacuum mixing system according to the invention with open feedthrough.
Figure 6:
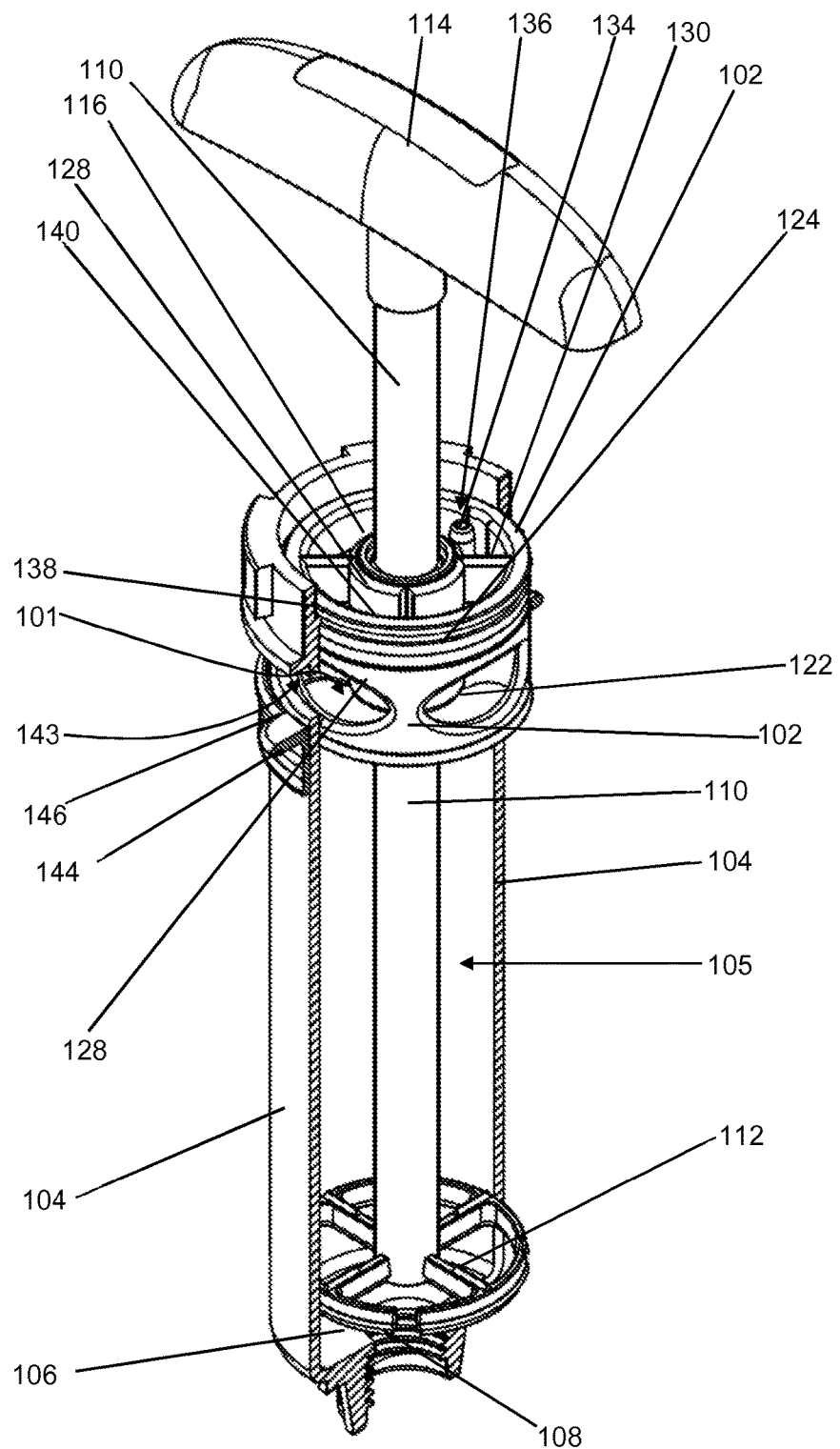
FIG. 6: shows a perspective partial sectional view of the vacuum mixing system according to FIG. 5 with open feedthrough.
Figure 7:
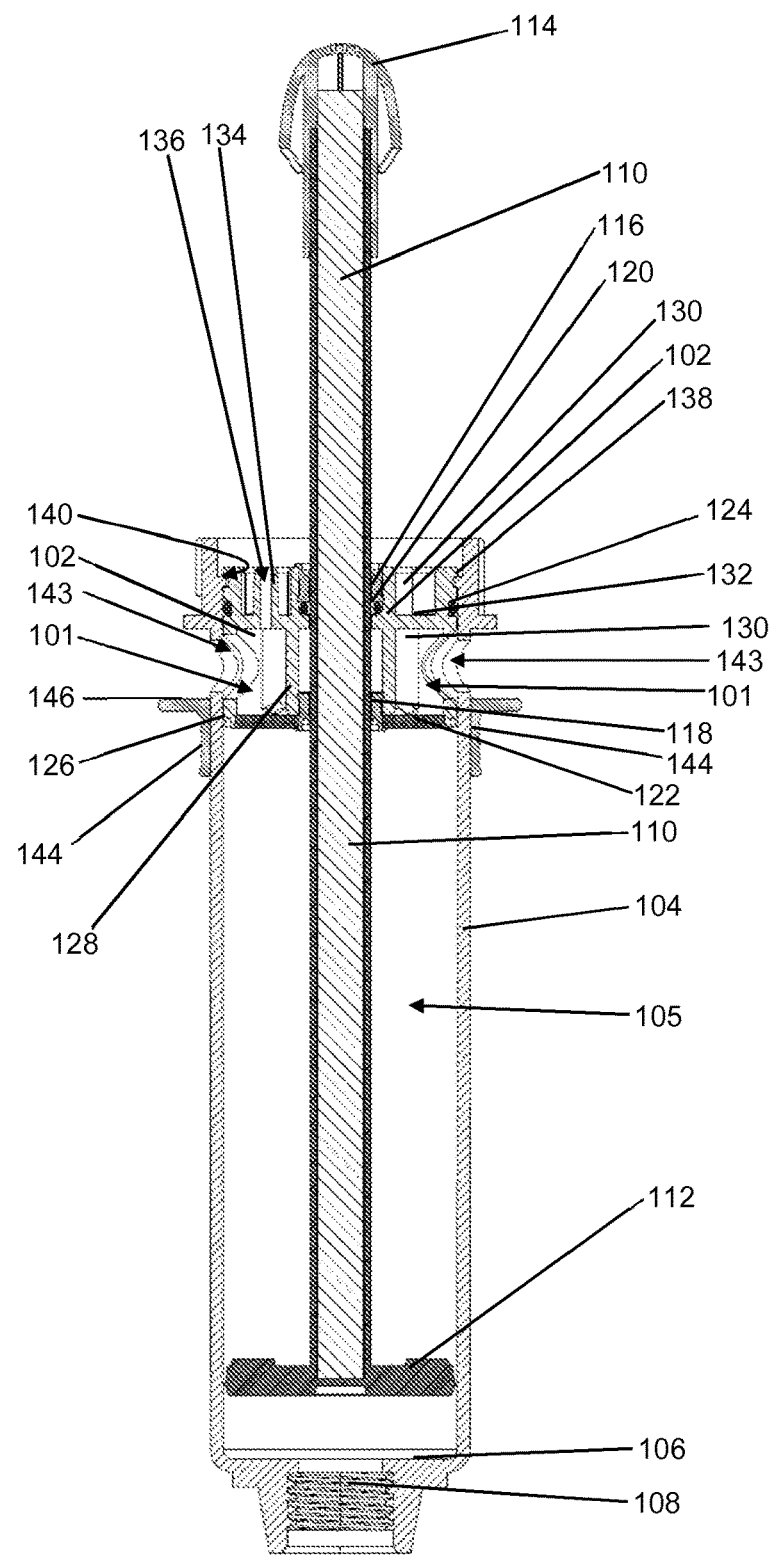
FIG. 7: shows a cross-sectional view of the vacuum mixing system according to FIGS. 5 and 6 with open feedthrough.
Figure 8:
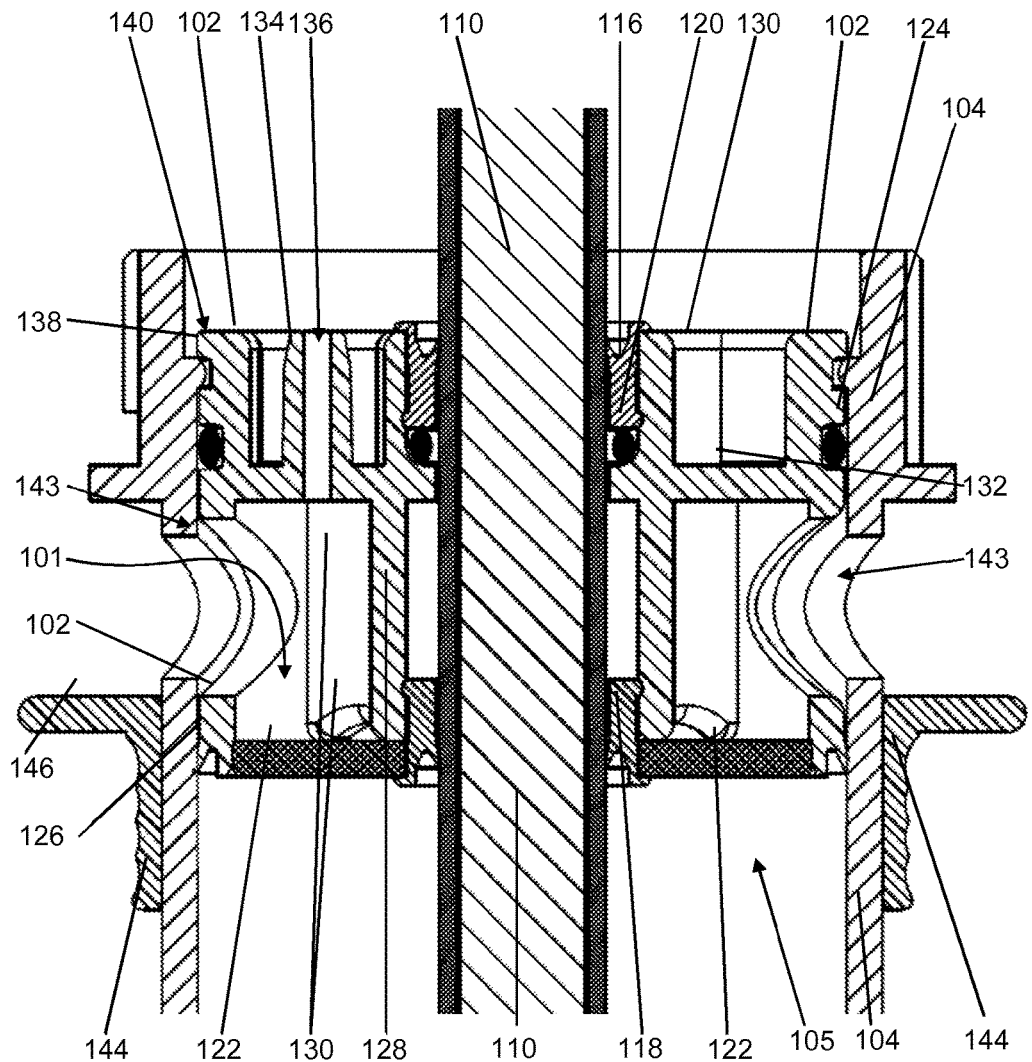
FIG. 8: shows a cross-sectional view of a detail of the vacuum mixing system according to FIGS. 5 to 7 with open feedthrough.
Figure 9:
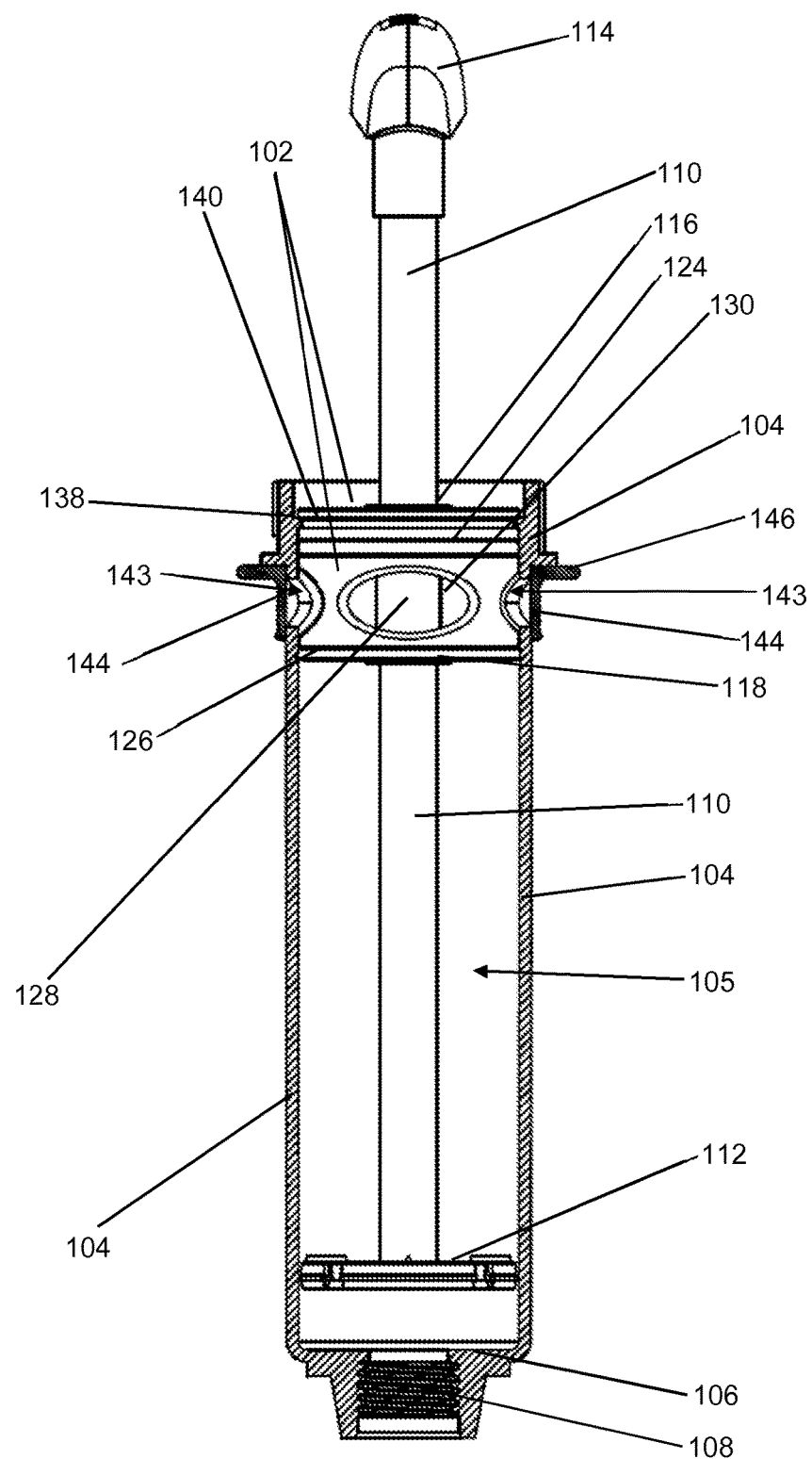
FIG. 9: shows a lateral partial sectional view of the vacuum mixing system according to FIGS. 5 to 8 with closed feedthrough.
Figure 10:
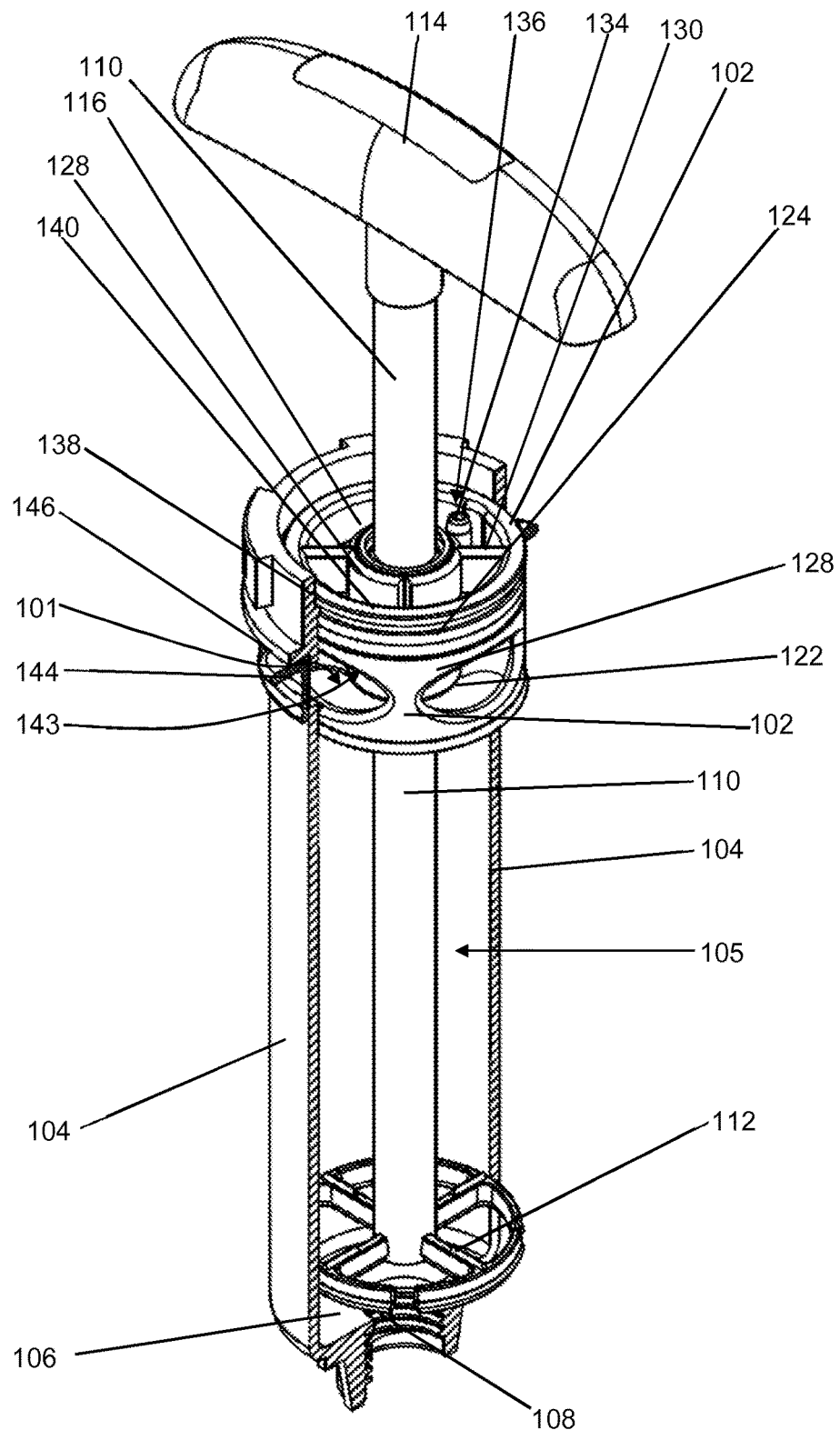
FIG. 10: shows a perspective partial sectional view of the vacuum mixing system according to FIGS. 5 to 9 with closed feedthrough.

FIGS. 5 to 8 show a second, alternative exemplary embodiment of the present invention and/or a second vacuum mixing system according to the invention, in which a feedthrough 101 through a largely cylindrical dispensing plunger 102 is open, and FIGS. 9 and 10 show the same alternative exemplary embodiment of the present invention and/or the second vacuum mixing system according to the invention, in which the feedthrough 101 through the dispensing plunger 102 is closed. In this context FIG. 5 shows a perspective external view, FIG. 6 shows a perspective partial sectional view, FIG. 7 shows a cross-sectional view, FIG. 8 shows a cross-sectional view of a detail, FIG. 9 shows a lateral partial sectional view, and capitalize 10 shows a perspective partial sectional view of the vacuum mixing system.

The design of this alternative embodiment is essentially similar to the design of the first exemplary embodiment.

The vacuum mixing system comprises a largely tube-shaped cartridge 104 having an internal space 105. The internal space 105 contains a cement powder (not shown) for producing a cement dough from two components. The cartridge 104 is closed on the front side (on the bottom in FIGS. 5 to 7 and 9 and not shown in FIG. 8) by means of a plate 106, in which an opening having an internal thread 108 is provided.

A baseplate (not shown) and/or a base (not shown) or a dispensing tube (not shown) for application of the ready-mixed cement dough can be mounted to the internal thread 108. Via the baseplate and/or the base, a second liquid container (not shown) containing a liquid monomer as second liquid component of the bone cement is connected to the cartridge 104 by means of a conduit (not shown). For this purpose, the conduit merges into a socket on the baseplate and/or base, whereby an external thread is provided on the socket thread such that the cartridge 104 can be or is screwed onto the socket by means of the internal thread 108 such that the conduit from the liquid reservoir can be or is connected via the conduit to the cartridge 104 in pressure-tight manner. A vacuum mixing system having a base of this type and/or a baseplate of this type, a conduit of this type, a socket of this type, and a liquid reservoir of this type is known, for example from DE 10 2009 031 178 B3 and/or U.S. Pat. No. 8,757,866 B2, such that reference shall be made to these patents for any details. For the discussion in the following, it shall be presumed that the front side of the cartridge 104 is initially closed towards the outside by the cartridge 104 being screwed onto a base of this type and/or a baseplate of this type of the vacuum mixing system by means of the internal thread 108.

The cartridge 104 is closed on the rear side (towards the top in FIGS. 5 to 10) by means of the dispensing plunger 102. A feedthrough in the dispensing plunger 102 has a rod 110 extend through it that ends on the front side in the internal space 105 of the cartridge 104 in a mixing element 112 that comprises four mixing vanes that extend radially in the direction of the wall of the cartridge 104. The rod 110 ends, on the rear side (on the top in FIGS. 5 to 7 and 9 and 10, and not shown in FIG. 8), in a handle 114 by means of which the rod 110 can be moved by hand. The rod 110 can be rotated about its axis and is stored in axial direction (shiftable in longitudinal direction) in the dispensing plunger 102. For this purpose, two bearing rings 116, 118 are provided in the dispensing plunger 102 and touch into the fit on the rod 110 and support the rod 110 as in a bearing.

The lower bearing ring 118 also serves to seal the internal space 105 in order to prevent powder or cement dough from exiting from the internal space 105. Moreover, in order to seal the internal space 105 in gas-tight and pressure-tight manner, a seal 120 in the form of an O-ring made of rubber is provided.

Since the rod 110 can be rotated by hand and shifted axially, the content of the internal space 105 can be mixed manually by means of the mixing element 112.

The feedthrough 101 through the dispensing plunger 102 is covered on the front side of the dispensing plunger 102 by means of a pore disk 122. The pore disk 122 prevents the cement powder from entering into the feedthrough 101 and/or the cement powder from exiting from the vacuum mixing system.

The external circumference of the dispensing plunger 102 has a circumferential seal 124 provided on it in the form of an O ring made of rubber by means of which the intervening space between the dispensing plunger 102 and the internal wall of the cartridge 104 is sealed and to allow the internal space 105 to be closed with respect to the outside in gas-tight and pressure-tight manner, when the dispensing plunger 102 is pushed and/or inserted into the cartridge 104, as is shown in FIGS. 5 to 10.

The dispensing plunger 102 comprises, on the front side, a circumferential wiper lip 126 by means of which, upon dispensation of a ready-mixed bone cement from the internal space 105 through the opening in the plate 106 by means of the dispensing plunger 102, all of the cement dough is propelled towards the front without any cement dough being squeezed from the internal space 105 past the wiper lip 126. The wiper lip 126 is deformed for this purpose. The wiper lip 126 is deformed from its original shape accordingly. Due to the elastic force arising in the process, the internal space 105 is sealed by the wiper lip 126. The same sealing principle, with respect to the rod 110 in this case, is also used for the lower bearing ring 118.

In the dispensing plunger 102, the rod 110 is guided through a sleeve 128 of the dispensing plunger 102. Four struts 130 of the dispensing plunger 102 extend radially from the sleeve 128 in the direction of the external circumference of the dispensing plunger 102. The struts 130 serve for mechanical stabilisation and shaping of the dispensing plunger 102 and for positioning of the pore disk 122. The dispensing plunger 102 is closed on the rear side between the openings in the jacket surface of the dispensing plunger 102 for the feedthrough 101 and the rear-side end of the dispensing plunger 102 (on the top in FIGS. 5 to 10) by a plate 132. The plate 132 is part of the dispensing plunger 102 and both are provided as a single part.

The vacuum feedthrough 134 that merges into a vacuum connector 136 in the form of a socket 136 is provided on the plate 132. A hose (not shown) can be plugged onto the vacuum connector 136 and can be connected to a vacuum source (not shown).

A circumferential spring 138 in the form of a ring 138 is provided in the internal circumference of the cartridge 104 and is provided as snap-in means 138 for locking the dispensing plunger 102 in the cartridge 104. A circumferential groove 140 and/or a circumferential recess 140 is provided in the dispensing plunger 102 as opposite snap-in means 140 such that the dispensing plunger 102 can be locked with respect to its mobility in longitudinal direction in the cartridge 104. Instead of the system consisting of groove 140 and spring 138, other locking means that can, for example, be deformed by hand and are thus easier to detach can be provided just as well without limiting the invention in any way or shape.

At least one opening 143 is provided in the wall of the cartridge 104 and, in the position of the dispensing plunger 102 shown in FIGS. 4 to 10, overlaps with the opening in the jacket surface the dispensing plunger 102 that leads to the feedthrough 101 through the dispensing plunger 102. A ring-shaped cuff 144 is provided as closure element 144 on the external circumference of the cartridge 104. Said cuff 144 has an internal circumference that is equal in size or slightly smaller than the external circumference of the cartridge 104 such that the cuff 144 fits on the cartridge 104. By means of projections 146 or handles 146, the cuff 144 can be moved along the cylinder axis of the cartridge 104 and can thus close the openings 143 in the wall of the cartridge 104.

Initially, the bone cement powder is filled into the cartridge 104 that is closed on the front plate 106. For this purpose, the dispensing plunger 102 is not yet inserted into the cartridge 104 initially. Subsequently, the dispensing plunger 102 is plugged into the cartridge 104 until the spring 138 locks to the groove 140. In this context, the cuff 144 does not cover the opening 143 and/or openings 143. Said opened position is shown in FIGS. 5 to 8. The entire cartridge 104 and/or the entire vacuum mixing system can be disinfected and/or sterilised in a chamber through the open feedthrough 101 and the opened opening 143 by evacuating the air from the surroundings of the cartridge 104 and/or of the vacuum mixing system and by filling the surroundings of the cartridge 104 and/or of the vacuum mixing system with ethylene oxide.

Subsequently, the cuff 144 is pushed over the opening 143. The cuff 144 closes the openings 143 or the opening 143 in the walls of the cartridge 104 towards the feedthroughs 101. The seal 124 closes the internal space 105, except for the vacuum feedthrough 136, in pressure-tight and gas-tight manner by the seal 124 touching against the internal walls of the cartridge 104.

A hose connected to a vacuum source is then connected to the vacuum connector 134. The air is drawn from the internal space 105 through the vacuum feedthrough 136. The pore disk 122 prevents powder from advancing from the internal space 105 into the vacuum system. Since the internal space 105 is pressure-tight, except for the conduit connected to the plate 106 and/or the internal thread 108 and the liquid container, the internal space 105 is being evacuated. Due to the vacuum in the internal space 105, the cuff 144 is pushed onto the opening 143 and/or is being aspirated and the opening 143 is effectively closed by this means. The conduit and the liquid reservoir of the vacuum mixing system are closed towards the outside in gas-tight and pressure-tight manner. The monomer is aspirated from the liquid reservoir through the conduit into the internal space 105. It is mixed with the cement powder in this location.

The cement powder can be mixed by hand with the monomer liquid in a vacuum by means of the mixing element 112 in the internal space 105 by rotating and pushing the rod 110 in and pulling it out. After the mixing took place, the cartridge 104 is unscrewed from the base and/or baseplate and a dispensing tube (not shown) is screwed onto the internal thread 108. The dispensing tube can contain a static mixer. The rod 110 can be pulled out of the internal space 105 all the way to the stop such that the mixing element 112 touches against the front side of the dispensing plunger 102. The rod 110 can be broken off at a predetermined breakage site (not shown) by means of the handle 114. Subsequently, the cartridge 104 can be inserted into an extrusion device (not shown) for propelling the dispensing plunger 102 in the cartridge 104, or the dispensing plunger 102 is propelled by means of a pestle (not shown). For example, the dispensing plunger 102 can be unlocked from its locked position and the dispensing plunger 2 is propelled in the cartridge 104 by the vacuum that is still being applied, since no vacuum, but rather ambient pressure, is now being applied outside the cartridge 104.

Propelling the dispensing plunger 102 causes the cement dough to be driven from the internal space 105 of the cartridge 104 and to be applied by means of the dispensing tube.

All parts of the vacuum mixing system are manufactured from plastics by injection moulding, whereby the seals 120, 124 preferably consists of rubber or another elastic plastic material.

The features of the invention disclosed in the preceding description and in the claims, figures, and exemplary embodiments, can be essential for the implementation of the various embodiments of the invention both alone and in any combination.

LIST OF REFERENCE NUMBERS

1, 101 Feedthrough
2, 102 Dispensing plunger
4, 104 Cartridge
5, 105 Internal space of the cartridge
6, 106 Plate
8, 108 Internal thread
10, 110 Rod
12, 112 Mixing element
14, 114 Handle
16, 116 Bearing/bearing ring
18, 118 Bearing/bearing ring
20, 120 Seal/O-ring
22, 122 Pore disk
24, 124 Seal/O-ring
26, 126 Wiper lip
28, 128 Sleeve
30, 130 Strut
32, 132 Plate
34, 134 Vacuum connector/socket
36, 136 Vacuum feedthrough
38, 138 Spring
40, 140 Groove/recess
42 Groove/recess
143 Opening in the cartridge wall
144 Closure element/cuff
146 Projection/handle

The invention claimed is:

1. Vacuum mixing system for the mixing of polymethylmethacrylate bone cement, comprising
   at least one cartridge (4, 104) having an evacuatable internal space (5, 105) for the mixing of the bone cement, whereby the internal space (5, 105) comprises a cylindrical swept volume defined by a cylindrical cartridge wall,
   a mixing element (12, 112) that is arranged in the internal space (5, 105) of the cartridge (4, 104) such as to be mobile and can be operated from outside the vacuum mixing system in order to mix the content in the internal space (5, 105) of the cartridge (4, 104), and
   a dispensing plunger (2, 102) having a cylindrical external circumference defining a jacket surface and a first base surface bordering a base surface of the internal space (5, 105) of the cartridge (4, 104) and which can be or is locked to the cartridge (4, 104) in detachable manner and which, in the detached state, is mobile in the cylindrical region of the internal space (5, 105) of the cartridge (4, 104),
   whereby a gas-permeable and particle-impermeable feedthrough (1, 101) is arranged in the dispensing plunger (2, 102) and said feedthrough (1, 101) is further formed between the dispensing plunger (2, 102) and the internal wall of the internal space (5, 105), whereby the feedthrough (1, 101) extends from an opening in the jacket surface of the dispensing plunger (2, 102) to an opening in the first base surface of the dispensing plunger (2, 102).

2. Vacuum mixing system according to claim 1, wherein the dispensing plunger (2, 102) comprises at least one circumferential seal (20, 120) that seals the internal space (5, 105) of the cartridge (4, 104) with respect to the outside, optionally having at least one circumferential seal (20, 120) arranged between a second base surface of the dispensing plunger (2, 102), which is situated opposite from the first base surface of dispensing plunger (2, 102), and the opening in the jacket surface of the dispensing plunger (2, 102).

3. Vacuum mixing system according to claim 1, wherein the cartridge wall of the cartridge (4, 104) comprises an opening (143), which overlaps with the opening in the jacket surface of the dispensing plunger (2, 102) while the dispensing plunger (2, 102) is in an opened position, and by means of which the internal space (5, 105) is or can be connected in gas-permeable manner to the surroundings of the vacuum mixing system.

4. Vacuum mixing system according to claim 3, wherein a closure element (144) is arranged on the external wall of the cartridge (4, 104) by means of which the opening (143) in the wall of the cartridge (4, 104) can be closed, optionally a closure element (144) arranged on the external wall of the cartridge (4, 104) that can be shifted in axial direction of the cartridge (4, 104).

5. Vacuum mixing system according to claim 4, wherein the closure element (144) is a circumferential cuff (144) that touches, to fit, against the external wall of the cartridge (4, 104) and can be shifted in axial direction of the cartridge (4, 104) in order to cover and thus close the opening (143) in the wall of the cartridge (4, 104), whereby, optionally, at least one handle part (146) is fastened on the cuff (144) and is provided for manual shifting of the cuff (144) on the external wall of the cartridge (4, 104).

6. Vacuum mixing system according to claim 1, wherein the dispensing plunger (2, 102), in a first lockable position, projects from the cartridge (4, 104) such that the opening in the jacket surface of the dispensing plunger (2, 102) is open, and in that the dispensing plunger (2, 102), in a second lockable position, is arranged deeper in the internal space (5, 105) of the cartridge (4, 104) such that the opening in the jacket surface of the dispensing plunger (2, 102) is closed by the internal wall of the cartridge (4, 104).

7. Vacuum mixing system according to claim 6, wherein a circumferential sealing element (20, 120) is arranged between the opening in the jacket surface of the dispensing plunger (2, 102) and the second base surface of the dispensing plunger (2, 102), which is situated opposite from the first base surface of the dispensing plunger (2, 102).

8. Vacuum mixing system according to claim 1, wherein a gas-permeable particle filter (22, 122) is arranged in the feedthrough (1, 101) and/or at the opening to the feedthrough (1, 101) in the jacket surface of the dispensing plunger (2, 102) and/or at the opening to the feedthrough (1, 101) in the first base surface of the dispensing plunger (2, 102), whereby the gas-permeable particle filter (22, 122) is impermeable for particles having a diameter of more than 1 μm.

9. Vacuum mixing system according to claim 1, wherein the dispensing plunger (2, 102) is gas-tight on its side that points from the interior of the cartridge (4, 104), except for a vacuum feedthrough (36, 136).

10. Vacuum mixing system according to claim 1, wherein the dispensing plunger (2, 102) comprises, on the first base surface, a gas-permeable pore disk (22, 122) that is supported by ribbing.

11. Vacuum mixing system according to claim 1, wherein the dispensing plunger (2, 102) can be pushed axially into the cartridge (4, 104) in order to dispense a bone cement dough, that has been mixed from a bone cement powder and a monomer liquid, through a dispensing opening on an end of the cartridge (4, 104) opposite from the dispensing plunger (2, 102), whereby the dispensing plunger (2, 102) optionally can be pushed axially into the cartridge (4, 104) after detaching a locking mechanism.

12. Vacuum mixing system according to claim 1, wherein a dispensing opening of the cartridge (4, 104) comprises a connecting thread (8, 108).

13. Vacuum mixing system according to claim 1, wherein the mixing element (12, 112) is arranged on a rod (10, 110) that is guided through a gas-tight passage into the interior of the cartridge (4, 104), and the mixing element (12, 112) is mobile by pushing it in and out of the cartridge (4, 104) and by rotating it in the cartridge (4, 104), whereby the rod (10, 110) optionally comprises a predetermined breakage site at which the rod (10, 110) can be broken off near the passage once it has been pulled out of the cartridge (4, 104).

14. Vacuum mixing system according to claim 1, wherein the vacuum mixing system comprises a glass container for monomer liquid, and the cartridge (4, 104) contains a cement powder, whereby an opening element for opening of the reservoir container is provided, and the cartridge (4, 104) is or can be connected via a conduit to the opened reservoir container.

15. Vacuum mixing system according to claim 14, wherein the vacuum mixing system comprises a base element, whereby the base element stores the cartridge (4, 104), the reservoir container, and the opening element.

16. Vacuum mixing system according to claim 15, wherein the base element comprises a coupling means for a non-positive fit- and/or positive fit-like connection to the connecting means (8, 108) on the dispensing opening of the cartridge (4, 104).

17. Vacuum mixing system according to claim 14, wherein a valve element controlling and/or triggering the outflow of the monomer liquid from the reservoir container into the cartridge (4, 104) is arranged in the conduit.

18. Vacuum mixing system according to claim 14, wherein a snap-in means (38, 138) is provided on the cartridge (4, 104) and at least one opposite snap-in means (40, 42, 140) is provided on the dispensing plunger (2, 102), whereby the dispensing plunger (2, 102) is detachably locked to the snap-in means (38, 138) in the cartridge (4, 104) in one position or is detachably locked in at least two positions, whereby the feedthrough (1, 101) is opened in a first locked position and is closed in gas-tight manner in a second locked position.

* * * * *